United States Patent
Hull et al.

[19]

[11] Patent Number: 5,874,237
[45] Date of Patent: Feb. 23, 1999

[54] METHOD AND APPARATUS FOR COLLECTING AIRBORNE BIOLOGICAL PARTICLES

[76] Inventors: Bryan Patrick Hull; Caren Pieper Hull, both of 182 Jackson Rd., San Bernadino, Calif. 92408

[21] Appl. No.: 599,749

[22] Filed: Feb. 12, 1996

[51] Int. Cl.[6] .................................................. C12Q 1/04
[52] U.S. Cl. ................................ 435/34; 435/4; 435/29; 435/287.1; 435/283.1
[58] Field of Search .................................. 435/4, 29, 30, 435/34, 283.1, 287.1, 288.7

[56] References Cited

U.S. PATENT DOCUMENTS

| | | | |
|---|---|---|---|
| 3,956,070 | 5/1976 | Kenyon | 195/103.5 |
| 4,092,221 | 5/1978 | Schlichting, Jr. | 195/127 |
| 4,230,031 | 10/1980 | Pedroso et al. | 422/104 |
| 5,500,369 | 3/1996 | Kiplinger | 435/309.1 |

*Primary Examiner*—Gary E. Hollinden
*Assistant Examiner*—Dameron Jones
*Attorney, Agent, or Firm*—Sherry J. Whitney

[57] ABSTRACT

A bioaerosol collection device (BCD) includes a housing with a first opening, a second opening, and a plate positioned between the first opening and the second opening. When a vacuum is applied to the second opening, the resulting air flow through the BCD causes bioaerosols to collect on a medium positioned on a surface of the plate. The collected bioaerosols are incubated and the resulting bacterial colonies can then be counted to determine a level of bioaerosol contamination in the air.

12 Claims, 3 Drawing Sheets

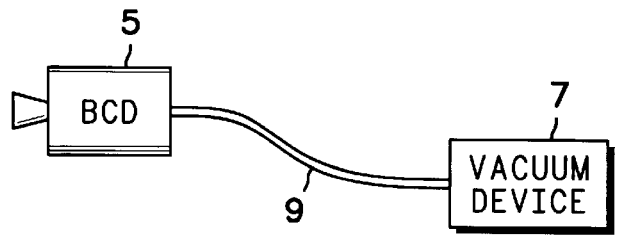
FIG. 1
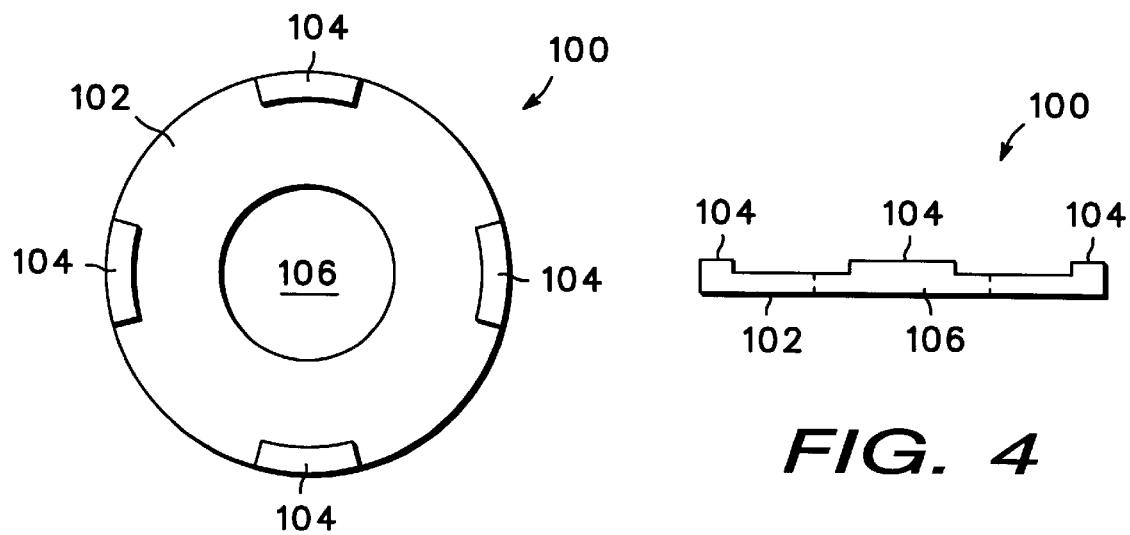
FIG. 3
FIG. 4
FIG. 5
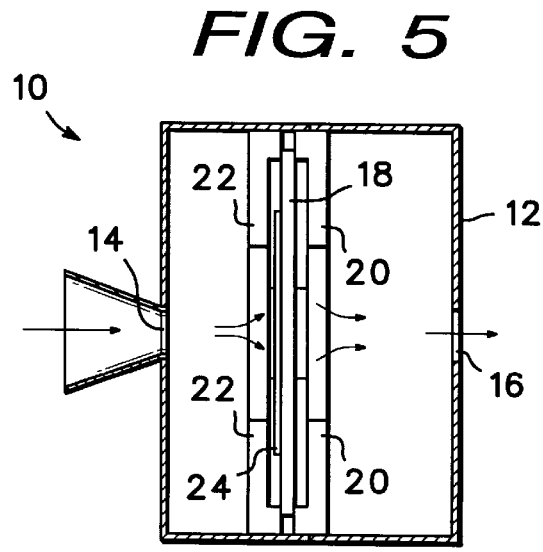

```
        BEGIN
          │
          ▼
   ASSEMBLE BCD ── 200
          │
          ▼
  PLACE BCD IN PROXIMITY ── 202
   TO AIR TO BE SAMPLED
          │
          ▼
    APPLY VACUUM ── 204
          │
          ▼
  COLLECT BIOAEROSOLS ── 206
          │
          ▼
   INCUBATE MEDIUM ── 208
          │
          ▼
        COUNT
    BACTERIAL COLONIES ── 210
          │
          ▼
         END
```

METHOD AND APPARATUS FOR COLLECTING AIRBORNE BIOLOGICAL PARTICLES

FIELD OF THE INVENTION

The present invention relates, in general, to measuring levels of airborne biological particles.

BACKGROUND OF THE INVENTION

Many contagious illnesses result from human inhalation of infectious, aerosolized particles. As used herein, an "aerosolized particle" is a particle which has become airborne within a liquid droplet or other airborne carrier (e.g., a dust particle). Infectious, aerosolized particles include bacterial cells, fungal spores, viruses, and other biological material. These infectious, aerosolized particles are referred to herein as "bioaerosols".

Viruses which can be transferred from human to human via an airborne route include rhinovirus, influenza virus, measles, rubella, and smallpox. Bacteria which can be transmitted via aerosols include staphylococcus aureus (staph infection) and legionella pneumonphila (Legionnaires disease). Aerosolized fungi can include, for example, Aspergillus which has been implicated as an airborne hazard in a hospital setting.

Infectious particles can become aerosolized, for example, when a person speaks, coughs, or sneezes. As more has been learned about the nature of infectious aerosols, researchers have discovered that various medical and dental procedures can generate bioaerosols as well. For example, infectious particles can become aerosolized when high-speed medical and dental machinery (e.g., dental scalers, bone saws, electrocautery procedures, and laser surgery) causes particle-containing droplets to be forced from a human or animal source. Infectious particles can also exist in vaporized water from cooling towers, water faucets, and humidifiers, for example. Spray irrigation which uses reclaimed waste-water also contains bioaerosols. Further, agricultural dust and airborne organic materials are likely to contain bioaerosols.

In order to protect humans and animals from preventable infectious illnesses resulting from the inhalation of bioaerosols, a need to detect and quantify bioaerosols exists. Detection and quantification of bioaerosols is an important first step in the identification and elimination of dangerous bioaerosols.

Several devices and methods for assessing airborne concentrations of viable microorganisms have been developed. Among the most simple of all methods is to place petri dishes with nutrient or selective media around the tested area. The bioaerosols attach to the surface of the nutrient agar plate and the level of bioaerosols in the environment can be inferred from the quantity on the plate.

Another method uses an Anderson Microbial Sampler (AMS) to collect bioaerosols. The AMS is a commercially available device having one, two, or six stages. For a multi-stage AMS, each successive stage has smaller through-holes. Because the through-hole size decreases with each stage, air drawn through the AMS accelerates at each stage. Less aerodynamic particles are trapped at the earlier stages.

A petri dish containing an agar medium appropriate for the microorganism being measured is placed in the AMS and a sample of air is drawn. The petri dish is then removed, inverted in its cover, incubated, and colonies enumerated.

The AMS enables particles to be sized aerodynamically, regardless of physical size, shape, or density. However, the AMS is relatively expensive. The expense of prior-art devices precludes widespread use of bioaerosol measurement devices, thus, the potential health benefits of such measurement devices generally remain unrealized What is needed is an apparatus for measuring bioaerosols which is inexpensive, accurate, and has a simple design. Further needed is a non-invasive, simple method for measuring bioaerosols using such a device.

BRIEF DESCRIPTION OF THE DRAWINGS

FIG. 1 illustrates a system for bioaerosol collection in accordance with a preferred embodiment of the present invention;

FIG. 3 illustrates a top view of a plate support structure in accordance with a preferred embodiment of the present invention;

FIG. 4 illustrates a side view of a plate support structure in accordance with a preferred embodiment of the present invention;

FIG. 5 illustrates a side, interior view of a BCD in accordance with a preferred embodiment of the present invention; and FIG. 6 illustrates a flowchart of a method for collecting and measuring bioaerosols in accordance with a preferred embodiment of the present invention.

DETAILED DESCRIPTION OF THE DRAWINGS

Figure 2:
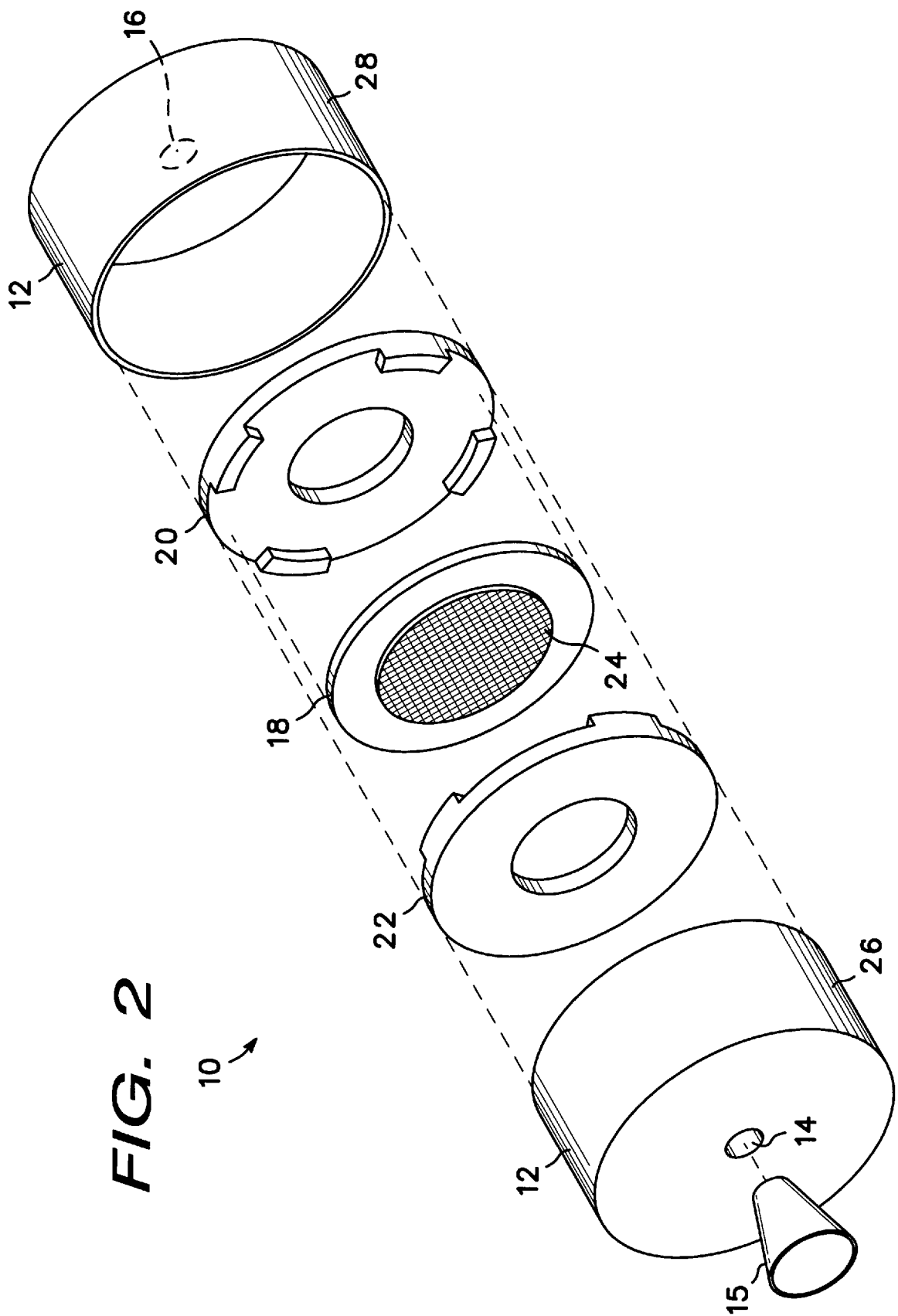
FIG. 2 illustrates an exploded view of a bioaerosol collection device (BCD) in accordance with a preferred embodiment of the present invention.

The method and apparatus of the present invention provides the ability to measure bioaerosol levels where the apparatus has a simple, inexpensive design. As used herein, the apparatus will be referred to as a "bioaerosol collection device" (BCD).

FIG. 1 illustrates a system for bioaerosol collection in accordance with a preferred embodiment of the present invention. The bioaerosol collection system includes BCD 5 connected to vacuum device 7 through tube 9. BCD 5 is a one-stage device which enables collection of airborne bioaerosols. The construction and operation of a preferred embodiment of BCD 5 are described in detail in conjunction with FIGS. 2–5. Vacuum device 7 is connected to BCD 5 through tube 9 and is used to draw air through BCD 5 such that bioaerosols contained within the air can be collected within BCD 5.

FIG. 2 illustrates an exploded view of bioaerosol collection device 10 (BCD) in accordance with a preferred embodiment of the present invention. In a preferred embodiment, BCD 10 includes housing 12, plate 18, medium 24, and plate support structures 20, 22. Housing 12 and structures 20, 22 can be made of almost any rigid material including, for example, plastic, metal, or glass. Housing 12 comprises at least two separable components 26, 28 which enable the interior cavity of housing 12 to be accessed so that plate 18 can be inserted and removed from housing 12.

In a preferred embodiment, plate 18 is a petri dish. As will be discussed below, during bioaerosol collection, plate 18 contains medium 24 which is appropriate for incubating biological material. In alternate embodiments, plate 18 could be any surface which is capable of holding an appropriate medium 24.

Plate support structures 20, 22 are separable from, coupled to, or integral with, housing 12 and are for supporting plate 18 in a position which allows air to flow across the surface of and beyond medium 24. Plate support structures 20, 22 are constructed in a manner which allows the air flow to occur. For example, plate support structures 20, 22 could have dispersed supports which provide air flow channels or plate support structures 20, 22 could be made of a porous material which enables air flow through BCD 10.

In a preferred embodiment, plate support structures 20, 22 are separable from housing 12. This enables plate 18 to be inserted between plate support structures 20, 22 during assembly of BCD 10. A preferred embodiment of plate support structures 20, 22 is depicted in FIGS. 3 and 4. Assembly of BCD 10 is described in conjunction with FIG. 6.

In alternate embodiments, one or both of plate support structures 20, 22 are coupled to or integral with housing 12. For example, plate support structure 22 could be coupled to or integral with separable component 26. Similarly, plate support structure 20 could be coupled to or integral with separable component 28. In another alternate embodiment, housing 12 could provide support for plate 18 without plate support structures 20, 22.

Plate support structure 22 provides a single stage which directs air flow onto the surface of medium 24. As just described, plate support structure 20 allows air to continue to be drawn beyond plate 18. In alternate embodiments, either or both structures 20, 22 could be functionally replaced with different types of support or air directing structures.

As described previously, housing 12 is comprised of separable components 26, 28 in a preferred embodiment so that plate support structures 20, 22 and/or plate 18 can be inserted and removed from housing 12 during assembly. In an alternate embodiment, housing 12 could be one unit having a slot or other opening which enables insertion and removal of plate support structures 20, 22 and/or plate 18. Where one or both plate support structures 20, 22 are coupled to or integral with housing 12, only plate 18 and a removable plate support structure (if any) would need to be inserted and removed.

Housing 12 includes first opening 14 and second opening 16. In a preferred embodiment, first opening 14 is coupled to structure 15 which is preferably designed to enable air easily to flow into housing 12. For example, structure 15 could be a cone shaped structure. In alternate embodiments, different shaped structures 15 or no structure 15 could be used. In a preferred embodiment, first opening 14 is located within first separable component 26, although this is not required. First opening 14 can be positioned within any portion of housing 12 as long as the air flow entering first opening 14 can be directed onto the surface of medium 24.

In a preferred embodiment, second opening 16 is positioned substantially opposite first opening 14 in second separable component 28 of housing 12. In alternate embodiments, second opening 16 could be positioned in any portion of housing 12 such that a substantial amount of an air flow from first opening 14 to second opening 16 can be diverted across and beyond plate 18.

Second opening 16 is adapted to connect to a vacuum device (e.g., vacuum device 7, FIG. 1). When the vacuum device is activated, air will flow into first opening 14, across the surface of medium 24, beyond plate 18, and out second opening 16. As the air passes across medium 24, bioaerosols within the air flow will collect on medium 24. As will be explained further in conjunction with FIG. 6, these bioaerosols can then be incubated and an accurate estimate of the level of bioaerosols in the air sample near the BCD can be determined.

Plate 18 holds medium 24 on which biological material can grow. Medium 24 can be non-specific (i.e., medium 24 supports the growth of multiple species of bacteria). Blood agar and nutrient agar media are examples of non-specific media Alternatively, medium 24 can be selective (i.e., medium 24 is species-selective and allows only certain biological species to grow). Selective media can contain antibiotics or additional agents which prevent growth of unwanted organisms. Any suitable medium can be used on plate 18.

One technique which can benefit from using BCD 10 is "plaque assay". Plaque assay uses an assay (e.g., blood) having an added bacterial virus as an indicator of aerosol dispersion. The assay can be medium 24 which is placed on a plate 18 and inserted into BCD 10. Prior to application of the vacuum in the BCD, the bacterial virus has been grown to confluency (e.g., in nutrient agar). During application of the vacuum, if a bacterial virus is captured onto the surface of medium 24, a zone of bacterial cell death will be evident on the surface of medium 24 after incubation. Plaque assay using a bioaerosol collection device (e.g., BCD 10) has not been performed in the prior art.

BCD 10 can be a relatively small device. Therefore, BCD 10 can be used in a manner which is non-invasive, for example, to any medical procedure which is being performed. Similarly, BCD 10 can be inconspicuously used in areas where bioaerosol measurements are desired. In addition, BCD 10 is simply designed and can be manufactured from inexpensive materials. Although the design of a preferred embodiment of BCD 10 facilitates reuse, the simplicity of the design of BCD 10 could make it practical for BCD 10 to be a disposable device. The inexpensiveness of BCD 10 makes it ideal for widespread use. BCD 10 can be used at times and in places where prior-art devices are either cost-prohibitive or overly-invasive.

FIG. 3 illustrates a top view of plate support structure 100 in accordance with a preferred embodiment of the present invention. Plate support structure 100 is comprised of disk 102 and raised supports 104. During operation of BCD 10 (FIG. 2), plate 18 is held in place by raised supports 104 on both plate support structures 20, 22 (FIG. 2). The diameter of plate 18 is smaller than the diameter of disk 102 in a preferred embodiment. When plate 18 is positioned on a plate support structure 100, raised supports 104 in conjunction with opening 106 in plate support structure 100 create a channel which allows air to flow around plate 18. In an alternate embodiment, opening 106 and second opening 16 (FIG. 2) could be the same opening. The air flow through BCD 10 is described in detail in conjunction with FIG. 5.

FIG. 3 shows four raised supports 104. In alternate embodiments, more or fewer raised supports 104 could be used. In still other alternate embodiments, raised supports 104 could be made of a porous material or a material having one or more channels through raised supports 104. In those alternate embodiments, raised supports 104 could create a whole or partial contiguous ring around disk 102. As described previously, in a preferred embodiment, disk 102 is used to support raised supports 104. However, disk 102 is not critical to the present invention. Where plate support structure 100 is coupled to or integral with housing 12 (FIG. 2), only raised supports 104 are required in order to support plate 18.

In alternate embodiments, where the cross-sectional shape of housing 12 is not circular, the circumference of plate support structure 100 would be formed into the shape of the interior cavity of housing 12.

FIG. 4 illustrates a side view of plate support structure 100 in accordance with a preferred embodiment of the present invention. Raised supports 104 protrude above disk 102 in order to provide an air channel. Raised supports 104 can be separable from, coupled to, or integral with disk 102 and can be manufactured from the same or a different material.

FIG. 5 illustrates a side, interior view of BCD 10 in accordance with a preferred embodiment of the present invention. As illustrated in FIG. 5, a vacuum device coupled to second opening 16 creates air flow through BCD 10. The air flow enters first opening 14. Plate support structure 22 holds plate 18 in position and causes the air flow to be diverted onto the surface and beyond medium 24. Plate support structure 20 also supports plate 18 and allows the air flow to be channeled out second opening 16.

FIG. 6 illustrates a flowchart of a method for collecting and measuring bioaerosols in accordance with a preferred embodiment of the present invention. In a preferred embodiment, the method for measuring bioaerosols uses a BCD substantially similar to that described in conjunction with FIG. 2, although the method could also be used with alternate embodiments of the BCD.

The method begins, by performing the step 200 of assembling a BCD (e.g., BCD 10, FIG. 2). In a preferred embodiment, assembling the BCD entails placing a plate (e.g., plate 18) with an appropriate medium (e.g., medium 24) between plate support structures (e.g., structures 20, 22). Then, the plate and plate support structures are placed into the interior cavity of the BCD and the BCD is closed (e.g., by connecting first separable component 26 and second separable component 28 together). As described previously, in a preferred embodiment, the BCD is manufactured such that the interior housing of the BCD can be accessed by separating a first section of the housing from a second section of the housing. In an alternate embodiment, the housing could be a single unit with a slot into which the plate and/or plate support structures are inserted. In another alternate embodiment, one or both of plate support structures 20, 22 could be coupled to or integral with housing 12 and would not need to be inserted into housing 12. In still another alternate embodiment, the BCD could be pre-assembled.

Next, step 202 is performed by placing the BCD in proximity to an air sample for which a bioaerosol measurement is desired. In a medical environment, for example, a bioaerosol measurement could be desired in an operatory room, a waiting room, or a laboratory. Bioaerosol measurements could be desired indoors or outdoors.

In step 204, a vacuum device is used to create an air flow through the BCD. In a preferred embodiment, the vacuum is applied such that the air flow rate is in the range of from 50 to 100 liters per minute (L/min), although a higher or lower air flow rate can be used. Excellent results have been obtained using an air flow rate of approximately 83.3 L/min. The air flow passes across the surface of the medium on the plate within the BCD and bioaerosols within the air are trapped on the medium.

Bioaerosols are collected in step 206. The vacuum is applied for a period of time sufficient for an adequate number of bioaerosols to collect on the medium. For example, a period of several minutes could be sufficient in an area of moderate bioaerosol contamination, although longer or shorter periods could also be sufficient.

After collection is complete, the plate and medium are incubated in step 208 so that colonies of the bioaerosol or bioaerosols can form. In a preferred embodiment, the plate is incubated from 24 to 48 hours, although incubation can be performed for more or less time. The incubation temperature can range from 35 to 40 degrees Celsius in a preferred embodiment, although higher or lower temperatures can be used. An incubation temperature of approximately 37 degrees has proved to produce excellent colonies.

In step 210, the quantity of bioaerosols is measured by counting the colonies on the medium. In a preferred embodiment, different classifications of micro-organisms are identified and counted separately so that the composition of differing bioaerosols in a particular air sample can be ascertained. The method then ends.

The results of the bioaerosol measurements obtained using the method and apparatus of the present invention can be used to identify and eliminate bioaerosols which pose health hazards to humans or animals.

In summary, a method and apparatus for measuring bioaerosols has been disclosed which achieves several advantages over the prior art. One advantage to using the method and apparatus of the present invention is that they provides a way to measure bioaerosols using a simple, inexpensive device and an uncomplicated bioaerosol collection method. Because the device is inexpensive, it can be used more extensively than prior-art collection devices so that more health hazards which result from bioaerosols can be detected and eliminated. Further, the method is non-invasive because the bioaerosol device is relatively small and portable.

While the principles of the invention have been described above in connection with specific apparatus, it is to be clearly understood that this description is made only by way of example and not as a limitation on the scope of the invention.

What is claimed is:

1. A bioaerosol collection device (BCD) comprising:
   a housing having an interior cavity, a first opening located at one part of the interior cavity, and a second opening located at another part of the interior cavity, wherein the second opening is connectable to a vacuum device which produces an air flow which moves into the first opening, through the interior cavity, and out the second opening,
   wherein the interior cavity supports a plate holding a medium for collecting bioaerosols, the plate being supported within the interior cavity such that the air flow flows across the medium and around the plate, enabling bioaerosols contained within the air flow to be collected onto the medium.

2. The BCD as claimed in claim 1, further comprising:
   a support structure within the housing and positioned between the first opening and the plate such that the air flow is directed onto a surface of the medium.

3. The BCD as claimed in claim 1, further comprising:
   at least one support structure within the housing for holding the plate in a position in which a surface of the medium is in the path of the air flow.

4. The BCD as claimed in claim 1, wherein the second opening is substantially opposite the first opening in the housing.

5. The BCD as claimed in claim 1, further comprising the plate, wherein the plate is inserted and removed from the interior cavity.

6. A system for collecting and measuring bioaerosols comprising:
   a bioaerosol collection device (BCD) having a housing with an interior cavity, a first opening located at one part of the interior cavity, and a second opening located at another part of the interior cavity, wherein the second opening is connectable to a vacuum device which produces an air flow through the interior cavity, the interior cavity supports a plate holding a medium for collecting bioaerosols, and the plate is supported within the interior cavity such that the air flow flows across the medium and around the plate, enabling bioaerosols contained within the air flow to be collected onto the medium; and the vacuum device coupled to the second opening for producing the air flow which moves into the first opening, through the interior cavity, across the medium, around the plate, and out the second opening, wherein the bioaerosols are collected when the vacuum device applies a vacuum to the second opening to produce the air flow, resulting in the bioaerosols collecting onto the medium.

7. The system as claimed in claim 6, wherein the vacuum device is for producing the air flow at a rate in a range from 50 to 100 liters per minute.

8. A method for collecting and measuring bioaerosols in an air sample comprising the steps of:

a) placing a bioaerosol collection device (BCD) in proximity to the air sample, wherein the bioaerosol collection device includes a housing having a first opening and a second opening, and a plate supported within the housing, wherein the plate holds a medium for collecting the bioaerosols, wherein the plate is positioned within the housing such that an air flow entering the first opening and exiting the second opening will flow across a surface of the medium and around the plate;

b) collecting the bioaerosols contained in the air flow onto the medium by applying a vacuum to the second opening to produce the air flow through the housing; and c) measuring the bioaerosols which collected on the medium during the collecting step.

9. The method as claimed in claim 8, wherein the step of collecting comprises the step of:

1) applying the vacuum such that the air flow is in the range of 50 to 100 liters per minute.

10. The method as claimed in claim 8, further comprising the step of:

d) assembling the BCD prior to the placing step a) by inserting the plate into the BCD.

11. The method as claimed in claim 8, wherein the measuring step comprises the steps of:

c1) removing the plate from the housing;

c2) incubating the medium; and c3) counting bacterial colonies which grew during the incubating step c2) from the quantity of collected bioaerosols on the medium.

12. The method as claimed in claim 8, wherein the medium contains a bacterial virus, and the measuring step c) comprises the step of:

c1) observing a zone of bacterial cell death on the surface of the medium in order to measure the quantity of the bioaerosols.

* * * * *